United States Patent [19]

Wattiez et al.

[11] Patent Number: 4,556,721

[45] Date of Patent: Dec. 3, 1985

[54] DERIVATIVES OF MERCUROBUTOL, AND THEIR APPLICATION TO THE PROTECTION OF SUPPORTS MORE PARTICULARLY IN TEXTILES

[75] Inventors: Daniel Wattiez; Roger Chatelin, both of Lissieu; Michel Bourgeois, Lyons, all of France

[73] Assignee: Centre Technique Industriel Styled: Institut Textile, France

[21] Appl. No.: 570,596

[22] Filed: Jan. 13, 1984

[30] Foreign Application Priority Data

Jan. 13, 1983 [FR] France .................................. 83 00442

[51] Int. Cl.[4] ................................ C07F 3/12
[52] U.S. Cl. .................................... 556/128; 252/8.6; 514/496
[58] Field of Search .......................................... 260/433

[56] References Cited

U.S. PATENT DOCUMENTS

| | | | |
|---|---|---|---|
| 2,252,705 | 8/1941 | Christiansen | 260/433 X |
| 2,502,382 | 3/1950 | Kaplan et al. | 260/433 |
| 3,174,898 | 3/1965 | Takahi et al. | 260/433 X |
| 3,501,283 | 3/1970 | Braxton | 260/433 X |
| 3,516,814 | 6/1970 | Wollensak | |

FOREIGN PATENT DOCUMENTS 458103  7/1945  Belgium .

OTHER PUBLICATIONS

Chemical Abstracts 80 108607u (1974).
Chemical Abstracts 81 151169k (1974).

*Primary Examiner*—Helen M. S. Sneed
*Attorney, Agent, or Firm*—Steele, Gould & Fried

[57] ABSTRACT

New mercurobutol derivatives characterized in that they comprise at least one functional group, bonded to the mercurobutol phenol ring, which functional group being capable of intervening in a polymerization or polyaddition reaction, and said derivatives having the bioactive properties of mercurobutol, even after such reaction.

These new derivatives can intervene in a grafting operation either as termination agent or a polymerization agent.

These new derivatives, when grafted on a support, give it protection against bacteria, mushrooms and other micro-organisms.

5 Claims, No Drawings

DERIVATIVES OF MERCUROBUTOL, AND THEIR APPLICATION TO THE PROTECTION OF SUPPORTS MORE PARTICULARLY IN TEXTILES

The present invention relates to biologically active products and more particularly products capable of protecting supports for example in textiles, against bacteria, mushrooms and other micro-organisms. The invention more specifically relates to mercurobutol, which is a wellknown bioactive, commonly used in the product known as Mercryl, as an 0.5% alcoholic solution.

The protection of supports, in textile in particular against external agents such as bacteria, mushrooms, etc., by incorporating thereto products with a specific activity against the said agents, is already well known. French Pat. No. 1274 388 describes many embodiments of such a protection, which use the grafting techniques, namely the copolymer-forming technique, from an existing macromolecular chain. Amongst grafted macromolecular products, there are two definite extreme categories which differ in the way the bioactive function operates. In the first category, the agent with the bioactive function is labile, it can easily become detached from the graft and be released into the surrounding medium. The protecting activity of these products spreads through the outside medium in contact with the support: but the protection only lasts a short time and does not withstand repeated washings of the support. In the second category, the agent containing the bioactive function is stable, it is for example bonded to the graft by a covalent bond, and therefore is not realeasable into the surrounding medium. These products have a protection-by-contact activity: the bacteria or mushrooms coming into contact with the products are destroyed by the bioactive functions of the support. The protection conferred by grafted bioactive products with stable function is permanent, and can withstand repeated washing and maintenance cycles.

Despite intensive research conducted in this field the products of the second category have not been developed to any significant extent; this could be due to the difficulty of finding a compound with a wide enough spectrum of activity which is capable of intervening in a grafting reaction.

A family of compounds has now been found, and this is the object of the present invention, which are mercurobutol derivatives, particularly suitable for permanent protection by grafting of supports such as in textiles. The elements of that family are characterized in that they comprise at least one functional group bonded to the mercurobutol phenyl ring, which group can intervene in a polymerization or polyaddition reaction, and in that they have the bioactive properties of mercurobutol, even after their intervention in said reaction.

Advantageously, the functional group is an allyl, vinyl, acryl, epoxy or isocyanate group.

Preferably, said group is situated in ortho-position of the hydroxyl radical of the mercurobutol phenol ring.

In the reaction of grafting the support requiring protection, the functional group can intervene in two possible ways: as a polymerization agent, or as a termination agent. When the mercurobutol derivative according to the invention acts as a polymerization agent, it becomes part of the graft, i.e. of the polymer chain which is fixed on the macromolecular structure of the support to be protected, either as sole constituent or in copolymerization. When the functional group acts as termination agent, it is used with another monomer which constitutes the main part of the graft, the mercurobutol derivative according to the invention fixing itself on the end of the polymer chain forming the graft.

After their intervention in the grafting reaction, the derivatives according to the invention still have the bioactive properties of the mercurobutol. The grafted support, consequently, retains these properties permanently since, as a consequence of the grafting, the mercurobutol derivative forms part of the actual structure of the support.

A particularly advantageous application of the invention consists in protecting textile materials, such as those used in hospitals or like communities, against the development of bacteria or mushrooms. Textile materials, whether they contain natural fibers or artificial or synthetic fibers or yarns, all have a graftable macromolecular structure. It is therefore always possible, depending on the components of the textile material to be protected, to determine a grafting reaction in which a mercurobutol derivative according to the invention can intervene for the purpose of permanently conferring to the textile material the bioactive properties of the mercurobutol. The textile material, being so grafted, can then be subjected to repeated washing cycles without losing its bioactive properties.

For any grafting expert, it is also very easy to control the grafting rate, and to some extent the length of the grafts: for example, it is possible to control the number of mercurobutol derivatives according to the invention which intervene in the reaction, and their distribution over the macromolecular structure of the support to be protected. This can vary between a single derivative according to the invention, bonded to grafts which are numerous but short, and multiple derivatives according to the invention forming part of grafts which are few in number but very long.

Grafting experts also know what functional group should preferably be selected in relation to the support to be grafted or to one of the constituents of said support: allyl, vinyl or acryl groups will be used to protect cellulosic-type supports, for example textile articles based on cotton, viscose or spun rayon, papers or nonwovens; epoxy and isocyanate groups will be used to protect resins, varnishes or paintings.

The invention will be more readily understood from the following example of embodiment. Mercurobutol is the common designation of orthochloromercuric p-tert-butyl phenol. The derivative according to the invention described hereinafter is the ortho-allyl derivative of mercurobutol. It is synthesized according to the following steps:

allyl bromide is reacted with a quantity of p-tert-butyl phenol dissolved in ethanol and potassium hydroxid, and allyl ether is obtained from the p-tert-phenol, and separated from the potassium bromide then an allyl transposition is conducted in a nitrogen atmosphere between 230° and 260° C. to obtain ortho-allyl p-tert-butyl phenol.

a chloro-mercurization is then conducted on this last compound with mercury acetate and hydrochloric acid to obtain the derivative according to the invention, i.e. ortho-allyl ortho-chloro mercuric p-tert-butyl phenol of formula:

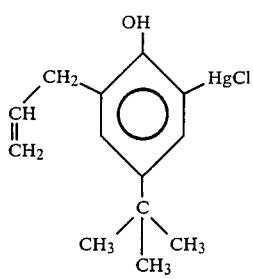

This derivative comprises an allyl group, bonded to the mercurobutol phenol ring, which allyl group is capable of intervening in the radical type polymerization reaction, by opening the double bond.

This derivative is caused to intervene in a grafting reaction on a textile material, containing no finishing agent and no bleaching agent, and composed in the proportion of 79% by weight of cellulose derivatives (75% viscose and 25% polynosic fibers) and 21% cotton covered elastodiene. This material is more particularly used as a restraining article required to exert a certain elastic pressure on a part of a patient's body. Acrylic acid is used for the grafting reaction in addition to the ortho-allyl derivative according to the invention, as main monomer of the graft formation. Activation of the support in order to create, on the macromolecular structure of the textile article, active sites for developing the grafting reaction, may be obtained by chemical or radiochemical route. Using the chemical route, and in the case of cellulose compounds, a ceric initiator, such as described in applicant's French Pat. No. 70 42410, is preferably used. When operating with an undistilled acrylic acid solution at 60% (8.3 moles per liter), it is possible to obtain grafts without homopolymer, the rate of which varies between 1 and 10%. Beyond that, the risks of obtaining homopolymer increase. The radio-chemical route uses an irradiation by accelerated electrons at 700 KeV, at dosis of 0.5 to 1 Megarad. The risks of homopolymer being lessened in this latter case.

The reaction bath is a mixture of acrylic acid and mercurobutol ortho-allyl derivative in the proportion of 1.5 to 3 g of the latter per liter of bath. With 1.5 g per liter, a mercury content of 0.204 mg per gram of treated material, is obtained after a two-hours long grafting reaction, initiated by ceric nitrate.

Comparative tests have been carried out to test the bioactive properties of the resulting grafted article, in the presence of a bacterial strain of Pseudonomas aeruginosa CIP A 22. The disk of material to be treated was placed on the bottom of a 250 ml-Erlenmeyer flask. 25 ml of peptonized water were introduced into the flask, in sterile conditions, so as to cover up the disk until the end of sampling withdrawals. A sterile control sample was placed in a first Erlenmeyer flask, and a control sample of the ungrafted material was placed in a second flask with 1 ml of the bacterial strain, whereas the grafted material with acrylic acid and the ortho-allyl derivative according to the invention was placed in a third flask. Periodical bacterial counts were conducted by taking 1 ml from each Erlenmeyer flask which was then incorporated to 10 ml of glucose-treated gelose in a Petri box; the colonies found after gelose homogenization and solidification and incubation for 72 hours at 30° C. being counted.

The results obtained are given in the following table:

|  | t = 0 | 2 h | 4 h | 6 h | 24 h | 48 h |
|---|---|---|---|---|---|---|
| Sterile control sample | 0 | 0 | 0 | 0 | 0 | 0 |
| Ungrafted article | 133 | 210 | 750 | 2100 | $>10^6$ | $0.5 \times 10^8$ |
| Grafted article | 106 | 27 | 18 | 2 | 0 | 0 |

The grafted article permanently retains the bioactive properties linked to the presence of the mercurobutol ring in the grafts. Repeated hard washings according to Norm NF 6 07.136 (Test 1A at 92° C. for 12 mins.) were conducted on a grafted article; the evolution of mercury on the article was observed: there was no mercury lost after two washes, and a loss of 5% after 5 washes.

According to another example of grafting reaction using the mercurobutol allyl derivative, polyurethane samples are treated either by irradiation in a beam of accelerated electrons at 700 KeV (the quantity received between 0.5 and 1 Megarad), or with ozone for about one hour. The samples are thereafter placed in a solution of acrylic acid (of 10 to 30%) and of allylmercurobutol in the proportion of 1 g per liter. In the case of treatment with ozone, it is necessary to heat for two hours at 100° C., but in the case of treatment by irradiation, the grafting develops at room temperature. The rates of mercury obtained are high, between 0.5 and 2 mg per gram of dry product, and the grafting rate is between 10 and 15%.

Contrary to certain grafted bioactive products, such as for example the copper-salified ones, the products using mercurobutol derivatives according to the invention are neither altered nor colored by the presence of bioactive grafts. This is a great advantage in the manufacture of articles for ready use, the color of which has to follow the fashion.

The invention is particularly advantageous in all cases where a support has to be protected against the action of agents such as bacteria or mushrooms, whether the support is a textile article, or a paper, a non-woven material, a painting or a plastic material: the sole requirement is that one of the support constituents can be grafted with a mercurobutol derivative according to the invention, with or without one or more other monomers.

The invention is also advantageous to protect a given medium against the action of bacteria or mushrooms. In this case, the support grafted with a mercurobutol derivative according to the invention is used as a protective barrier, the liquid or gaseous medium to be protected being caused to pass through said support which acts as a mechanical barrier holding back agents of a certain size, but the action of which is mainly to use its bioactive functions to destroy the agents coming into contact with the grafted support. Such a protective barrier will thus accept much greater flowing rates of the medium to be treated than in the case of an ungrafted support of equal protective efficiency.

What we claim is:

1. A mercurobutol derivatives of the formula:

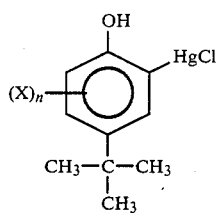

wherein n is 1 or 2 and x is a fucntional group selected from the group consisting of allyl, vinyl, acryl, and epoxy, said functional group being capable of participating in a polymerization or polyaddition reaction, and said derivatives having the bioactive properties of mercurobutol after said polymerization or polyaddition reaction.

2. The mercurobutol derivative of claim 1, wherein said functional group is a termination agent.

3. The mercurobutol derivative of claim 1, wherein said functional group is a polymerization agent.

4. The mercurobutol derivative of claim 1, wherein n is 1 and the single functional group is in the ortho-position of the hydroxyl radical of the mercurophenol ring.

5. The mercurobutol derivative of claim 1 having the formula:

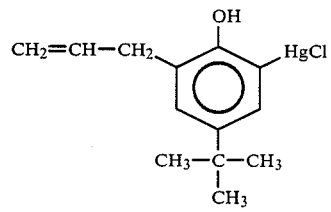

* * * * *